United States Patent [19]

Chin

[11] Patent Number: 5,222,958

[45] Date of Patent: Jun. 29, 1993

[54] APPARATUS FOR REMOVING PRE-PLACED PROSTHETIC JOINTS

[75] Inventor: Albert K. Chin, Palo Alto, Calif.

[73] Assignee: Zimmer, Inc., Warsaw, Ind.

[21] Appl. No.: 857,138

[22] Filed: Mar. 25, 1992

Related U.S. Application Data

[60] Division of Ser. No. 467,742, Mar. 1, 1990, Pat. No. 5,108,402, and a continuation-in-part of Ser. No. 255,650, Oct. 11, 1988, Pat. No. 4,919,153.

[51] Int. Cl.⁵ .............................................. A61F 5/04
[52] U.S. Cl. ..................................... 606/99; 606/100
[58] Field of Search ...................... 606/99, 69, 73, 61, 606/86

[56] References Cited

U.S. PATENT DOCUMENTS

| Re. 33,348 | 9/1990 | Lower | 606/73 |
|---|---|---|---|
| 2,570,465 | 10/1951 | Lundholm | 606/73 |
| 3,103,926 | 9/1963 | Cochran et al. | 606/73 |
| 4,059,102 | 11/1977 | Devas | 606/73 |
| 4,723,541 | 2/1988 | Reese | 606/73 |
| 4,858,601 | 8/1989 | Glisson | 606/73 |
| 4,963,144 | 10/1990 | Huiene | 606/73 |
| 5,061,271 | 10/1991 | Van Zile | 606/99 |

*Primary Examiner*—David Isabella
*Attorney, Agent, or Firm*—Todd A. Dawson

[57] ABSTRACT

A method and apparatus for removing a pre-placed prosthetic joint from a bone cavity and conditioning the cavity for receipt of a replacement joint. The pre-placed joint is first pulled from the mantle of hardened cement holding it within the cavity, thus leaving a cavity within the mantle. A mass of fluid cement is then placed within the cement cavity, after which a pulling tool is inserted into the fluid cement and the fluid cement is permitted to cure to bond with the hardened cement and form an integral mass. The pulling tool has helical screw thread on it, with means to connect a slap-hammer to its proximal end, so that its insertion into the fluid cement defines a threaded passageway. The pulling tool is then partly removed from the passageway by unscrewing it. Tension is then applied to the pulling tool to remove the tool and the cement mantle surrounding it from the bone cavity. The tool is then reinserted and the process is repeated as many times as desired until all of the cement mantle is removed. Alternatively, multi-piece tools may be used so that when the tool is partly removed from the mantle, a portion of the tool remains behind for later use, thus saving the step of reinserting the tool.

5 Claims, 7 Drawing Sheets

APPARATUS FOR REMOVING PRE-PLACED PROSTHETIC JOINTS

This is a division of application Ser. No. 07/467,742 filed Mar. 1, 1990 now U.S. Pat. No. 5,108,402, and a continuation-in-part of application Ser. No. 255,650, filed Oct. 11, 1988 now U.S. Pat. No. 4,919,153.

BACKGROUND OF THE INVENTION

1. Field of the Invention

The present invention relates to the replacement of pre-placed prosthetic joints and more particularly to a method and apparatus for removing the cement mantle used to secure the pre-placed joint in place. In its more particular aspects, the invention is concerned with such a method and apparatus for removing the cement mantle to secure the ball of a prosthetic hip joint to the patient's femur.

Prosthetic hip and knee joints have become relatively commonplace. Unfortunately, however, there has also been a progressive rise in the incidence of the nonseptic failure of such joints which necessitates revision surgery to affect their replacement. The leading cause of the nonseptic failure of hip joints is the loosening of the femoral side of the prosthetic appliance. This is generally the result of loosening of the cement securing mantle for the appliance from the cavity in the femur within which the mantle is received.

Revision surgery for the replacement of a failed joint requires that both the prosthetic appliance and the mantle holding it in place within the bone cavity be removed. The old prosthetic device is usually easily removed using a slap-hammer, since its surface is smooth and separable from the underlying cement mantle. The cement mantle, however, is tightly adherent to the surrounding bone and generally remains so adhered, even after the prosthetic device is removed.

2. Description of the Relevant Art

Removal of the adhered cement mantle is presently performed by progressively chipping the mantle away using a hammer and chisel. This method is tedious and the possibility of the chisel going past the mantle and fracturing the underlying bone is present. Other methods of removing the cement mantle, using powered drilling and boring devices, are similarly tedious and dangerous to the bone.

Prior revision surgery for the replacement of prosthetic hip joints also often includes a trochanteric osteotomy to remove the greater trochanter. Although this exposes the cement mantle and makes it easier to work upon, it generally does not eliminate the necessity for chipping the mantle away with a hammer and chisel to affect its removal.

Methylmethacrylate cement is the most accepted type of cement used to secure prosthetic joint appliances to bone. This cement is supplied to the surgeon packaged in two sterile components. One component is a liquid methyl methacrylate monomer and the other is a finely divided powder mixture of polymethyl methacrylate, methyl methacrylate-styrene-copolymer. At the time of use, the powder and liquid are mixed, resulting in the exothermic polymeric formation of a soft pliable dough-like mass. As the reaction progresses, within a few minutes a hard cement-like complex is formed. It is this complex which forms the cement mantle which the present invention is designed to remove.

Old hardened methylmethacrylate cement is capable of being partially dissolved and softened by the application of new like fluid cement thereto. The resulting composite of old and new cement cures into an integral bonded composite, generally within about ten minutes. Although the present invention relies upon this characteristic of methylmethacrylate cement, it may find equal application to other cements, so long as an adequate bond is provided between the old and new cement.

In the method of the invention described in the parent application, Ser. No. 255,650, a mass of new fluid methylmethacrylate cement is placed in contact with the hardened mantle of old methylmethacrylate cement desired to be removed. A pulling appliance is then imbedded within the fluid cement and the mass of cement is permitted to cure and harden, thus forming a bond between the appliance and the mantle of old cement. Tension is then applied to the pulling mantle to pull the appliance and the entire bonded mantle from the bone.

While this method is an improvement over the other prior art, it still suffers from a significant problem. In some patients, particularly those of advanced age, the bones may become brittle, and the application of sufficient force to dislodge the entire hardened mantle of cement may shatter part of the surrounding femur.

SUMMARY OF THE INVENTION

The present invention overcomes this problem by creating a hardened mantle by filling up the old mantle with new cement, as in the parent application, but then provides for removal of the entire hardened mantle in two or more pieces, rather than in a single unit. This allows each piece to be removed by the application of a lesser amount of force than would be needed to remove the entire mass at once, so that the force applied should not be great enough to shatter the surrounding bone.

The pulling tools of the present invention all comprise rigid posts of generally cylindrical configuration having an outer surface with helical screw threads, although it is possible that other outer surfaces could be used. The proximal end of each tool is provided with means to secure a slap-hammer thereto. In the preferred embodiments, the distal end of each tool is a cylinder of smaller diameter than the post, also bearing helical screw threads. In different embodiments, the distal end may be fixed on the tool, or may be detachable.

The nonobviousness of the present invention becomes particularly apparent when it is appreciated that the concept of adding cement to a mantle desired to be removed was not recognized until the invention of the parent application The normal current practice is only to remove material, as for example by chipping it away. The thought of adding new material naturally engenders the concern that it will aggravate the situation by increasing the mass of material which must be removed and making it less accessible to conventional removal instruments. Even the parent application teaches only removing the hardened mantle in a single piece, not in several pieces as taught in the present invention.

A principle object of the present invention is to provide an improved method and apparatus for removing a cement mantle from adhered condition within a bone cavity.

Another object of the invention is to provide such a method and apparatus which enables the mantle to be removed in pieces, without the application of a force great enough to break the surrounding bone.

Still another object of the invention is to provide such a method and apparatus which avoids the necessity of chipping away at the mantle to effect its removal.

Another and more general object of the invention is to provide such a method and apparatus which enables the removal of the mantle quickly and efficiently, with a minimum of trauma to the patient being treated.

A further general object of the invention is to provide such a method and apparatus which minimizes the risk of damage to the bone from which the mantle is being removed.

The features and advantages described in the specification are not all inclusive, and many additional features and advantages will be apparent to one of ordinary skill in the art in view of the drawings, specification and claims hereof. Moreover, it should be noted that the language used in the specification has been principally selected for readability and instructional purposes, and may not have been selected to delineate or circumscribe the inventive subject matter, resort to the claims being necessary to determine such inventive subject matter.

DETAILED DESCRIPTION OF THE PREFERRED EMBODIMENTS

FIGS. 1 through 29 of the drawings depict various preferred embodiments of the present invention for purposes of illustration only. One skilled in the art will readily recognize from the following discussion that alternative embodiments of the structures and methods illustrated herein may be employed without departing from the principles of the invention described herein.

Figure 1:
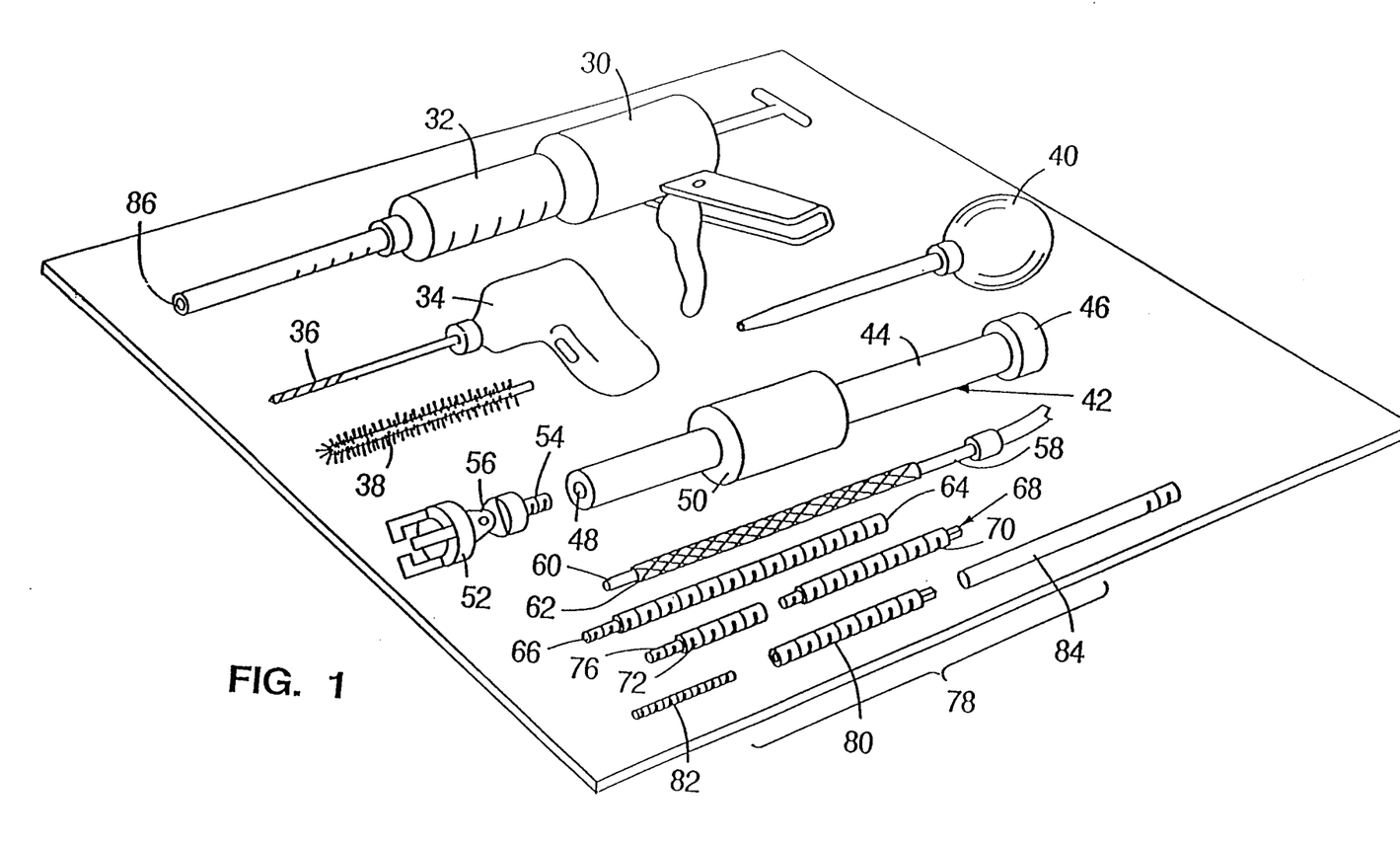
FIG. 1 is a perspective view illustrating the kit of equipment used to practice the method of the invention.

The kit shown in FIG. 1 includes the following components: injection gun 30 having a cement cartridge 32 secured thereto; rotary drill 34 having a drill bit 36 secured in the chuck thereof; brush 38 adapted to be secured to the chuck of the drill 34 in place of the drill bit 36; irrigation syringe 40; slap-hammer 42 having a cylindrical shaft 44 with a stop 46 on the distal end thereof, a screw threaded socket 48 in the proximal end thereof, and an annular weight 50 slidably received thereon for abutting engagement with the stop 46; a ball clamp 52 having a screw threaded shaft 54 secured thereto by an articulated joint 56, said shaft being designed for threaded engagement in the socket 48 of the slap-hammer 42; a suction tube 58 having a cover 60 of a moisture-absorbent material such as felt and a distal tip 62 of small diameter; a first pulling tool 64 having a distal end 66 of reduced diameter; a second pulling tool 68 which is comprised of two parts, a first portion 70, and a second portion 72 which is detachable from joint 74 and has a distal end 76; and a third pulling tool 78 which is comprised of a first portion 80 containing within its distal end a threaded receptacle, a second portion 82 which is threaded to screw into the threaded receptacle of the first portion 80, and a connecting rod 84.

Except for the pulling tools, all of the instruments in the kit are conventional. The pulling tools are especially designed for use in the method of the present invention. While the cement cartridge 32 is conventional, it is specifically chosen to have a narrow snout 86 for insertion into the cavity of the cement mantle intended to be removed.

Figure 10:
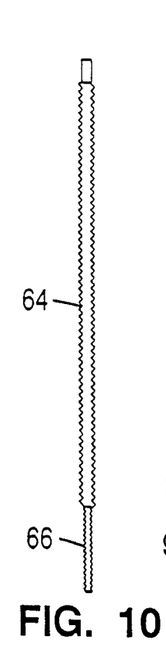
FIG. 10 is an elevational view of a first pulling tool constructed according to one embodiment of the present invention.

As shown in FIG. 10, the first pulling tool 64 has a length and cross section sufficient to enable it to be extended to the bottom of the cavity in the mantle in which it is intended to be used, without imparting lateral forces to the wall of the cavity. The appliance may be fabricated of any suitable high tensile strength corrosion-resistant material, such as stainless steel.

The pulling appliance provides a rigid post of cylindrical configuration having helical screw thread formed around it. The proximal end is screw threaded for receipt in the socket of the slap-hammer 42. The distal end 66 is axially aligned with the proximal end and is also cylindrical, but of reduced diameter compared to the proximal end, and also has a helical screw thread formed around it of the same pitch as the thread around the proximal end. As can be seen from FIG. 11, the distal end serves as a stop to limit the degree to which the pulling instrument may penetrate the cavity in the cement mantle. Its reduced cross-section assures that it may be inserted as far down into the cavity in the cement mantle as is necessary to remove the entire mantle, as will become more apparent from the following description of the method.

Figures 18, 19, 20, 21:
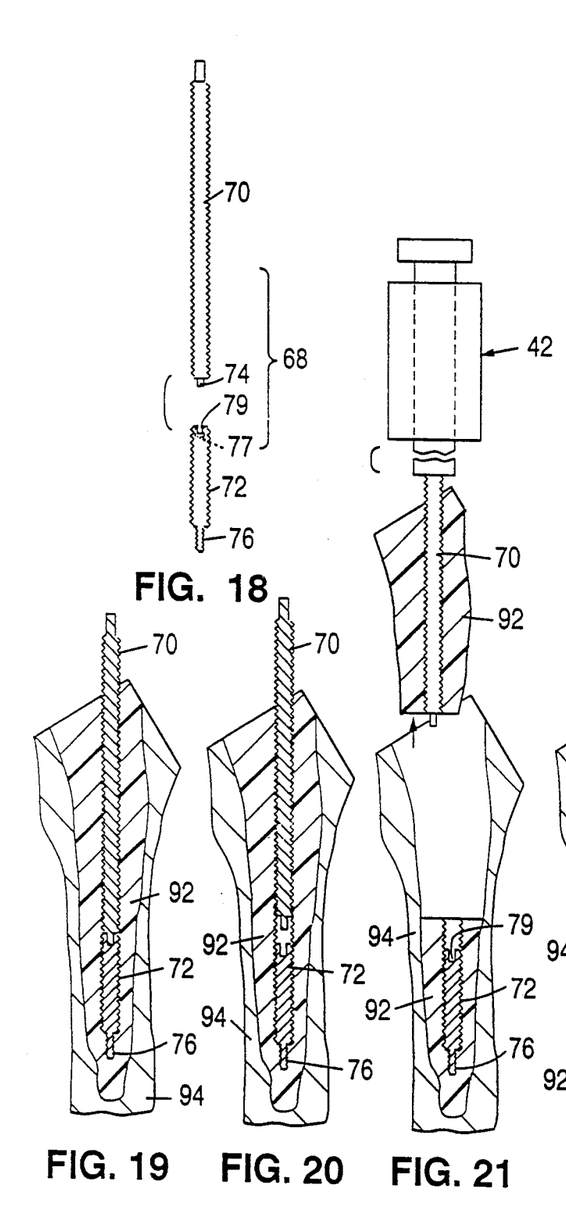
FIG. 18 is an elevational view of a second pulling tool constructed according to one embodiment of the present invention.
FIG. 19 is a cross-sectional elevational view similar to FIG. 11, illustrating the step of placing the second pulling tool within the fluid cement.
FIG. 20 is a cross-sectional elevational view similar to FIG. 19, illustrating the step of partly removing the second pulling tool from the hardened cement and separating the proximal and distal portions of the tool.
FIG. 21 is a cross-sectional elevational view similar to FIG. 20, illustrating the step of using a slap-hammer to apply tension to the cement mantle trough the pulling tool and removing a potion of the cement mantle from the femur.

FIG. 18 shows the second pulling tool 68. It is of essentially the same configuration as the first pulling tool 64, with the exception that it may be separated into two portions, a proximal first portion 70 and a middle second portion 72. A distal portion 76, which corresponds to distal portion 66 of the first pulling tool, is fixed to and extends from the second portion 72. The first portion 70 has at its distal end a cylindrical fitting or extension 74. Second portion 72 has at its proximal end a recess 77, formed for frictional receipt of the fitting 74, such that the portions 70 and 72 may be held together. Grooves 79 are formed in opposite sides of the recess 77 so that the second portion 72 can be turned by a screwdriver once first portion 70 is removed.

Figures 24, 25, 26:
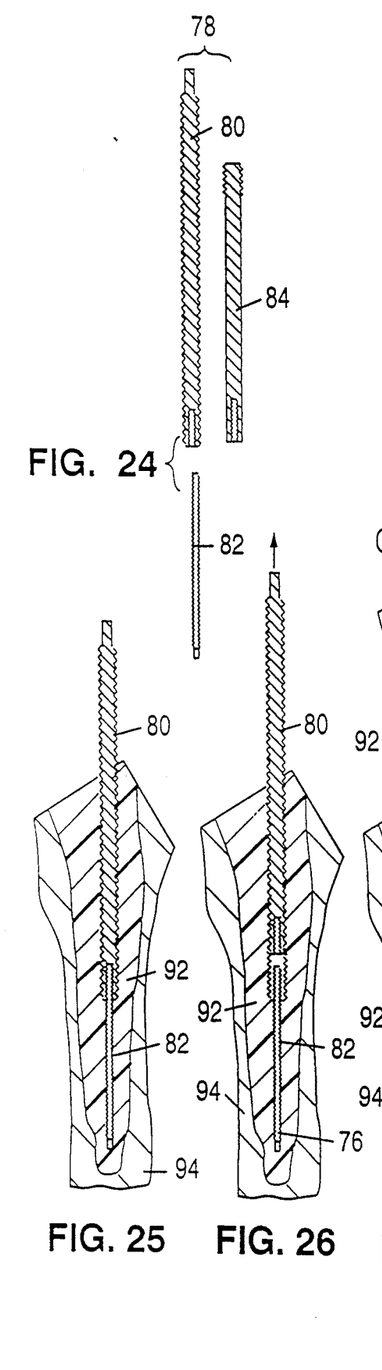
FIG. 24 is an elevational view of a third pulling tool constructed according to one embodiment of the present invention.
FIG. 25 is a cross-sectional elevational view similar to FIG. 11, illustrating the step of placing the third pulling tool within the fluid cement.
FIG. 26 is a cross-sectional elevational view similar to FIG. 25, illustrating the step of partly removing the third pulling tool from the hardened cement and detaching the distal end of the tool.

When assembled, the third pulling tool 78 is again of a similar configuration to the first pulling tool 64. In this case, however, the proximal first portion 80 has within it a threaded receptacle into which the distal portion 82 may be screwed. A connecting tool 84 is provided to secure the first portion 82 to the slap hammer 42. The tool 84 has a threaded receptacle for receiving distal portion 82 and a helical thread on its proximal end for receipt in the socket of the slap-hammer 42. The remainder of the connecting tool 84 is smooth, and is of a diameter smaller than the inside diameter of the threads on the first portion 80.

Figures 2, 3:
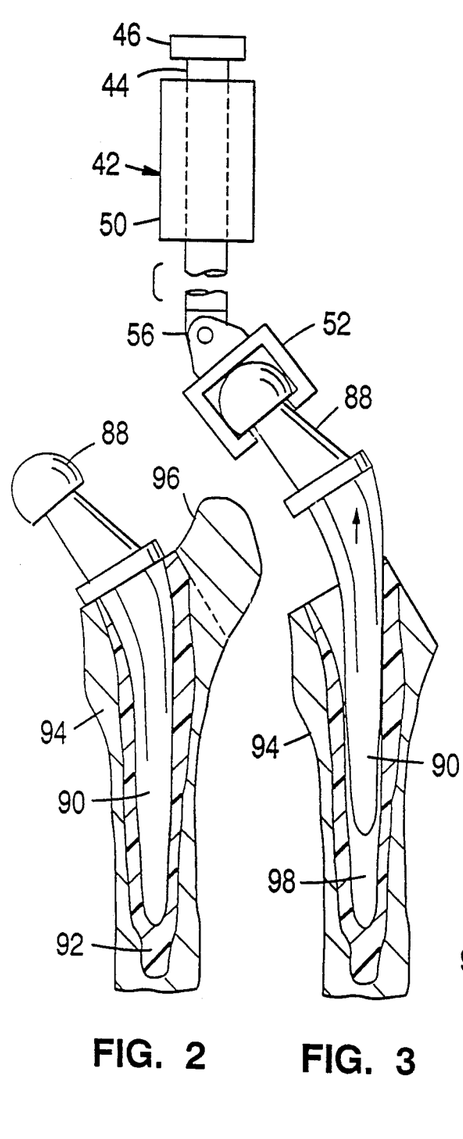
FIG. 2 is a cross-sectional elevational view of the upper femur of a leg with the femoral component of a prosthetic hip joint secured therein, and a dashed line showing the step of removing the greater trochanter from the femur.
FIG. 3 is a cross-sectional elevational view similar to FIG. 2, illustrating the step of removing the femoral component of the prosthetic hip joint from the cement mantle within the femur.

FIGS. 2 through 17 sequentially illustrate the steps of one method in removing the femoral component 88 of a hip joint and then removing the cement mantle 92 therefor from the femur 94. As shown in FIG. 2 femoral component 88 has been secured to the femur 94 through the cement mantle 92 in conventional manner. The problem to be solved by the present invention is the removal of the mantle without the use of excessive force, so that the joint can be renewed without damaging the femur 94.

FIG. 2 shows the preparatory step of removing the trochanter 96 of the femur. The dashed line in FIG. 2 designates the saw line for the trochanteric osteotomy used to remove the trochanter. This line is chosen so as to intersect the mantle 92, while at the same time leaving a sufficient bone interface so that the trochanter may be reattached to the femur. Removing the trochanter in this fashion increases access to the mantle 92 and aids in assuring that pulling of the mantle from the femur will not damage the bone structure.

FIG. 3 shows the step of pulling the femoral component 88 from the mantle 92. For this purpose, the ball clamp 52 is secured to the component and the slap-hammer 42 is attached to the clamp through means of the articulated joint 56. Once the clamp and hammer are so connected, the position of the hammer is adjusted so that its axis is generally parallel to the axis of the femoral component extension 90. The weight 50 is then slid along the slap hammer to impact with the stop 46, thus applying impact tension to the femoral component and pulling it from the mantle 92, as indicated by the arrow lines in FIG. 3. Removal of the femoral component from the mantle leaves a cement cavity 98.

Figures 4, 5:
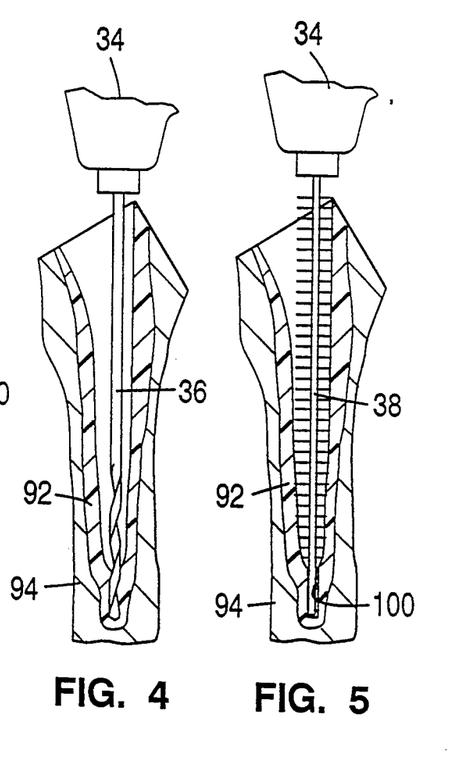
FIG. 4 is a cross-sectional elevational view similar to FIG. 3, illustrating the step of drilling out an extension in the bottom of the cavity left in the cement mantle by removal of the femoral component of the hip joint.
FIG. 5 is a cross-sectional elevational view similar to FIG. 4, illustrating the step of using a rotary brush to abrade the cavity within the cement mantle.
Figures 6, 7:
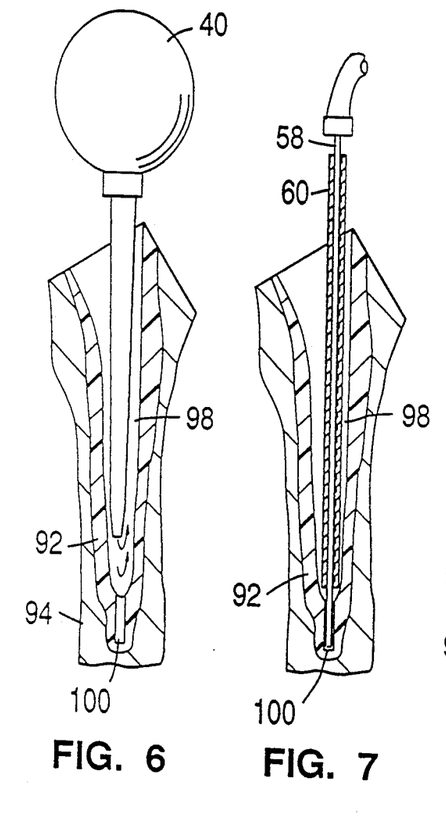
FIG. 6 is a cross-sectional elevational view similar to FIG. 5, illustrating the step of irrigating the cavity within the cement mantle.
FIG. 7 is a cross-sectional elevational view similar to FIG. 6, illustrating the step of removing any remaining moisture from the cavity in the cement mantle by use of a suction tube.

FIGS. 4 to 7 show the steps of drilling and cleaning the interior of the cavity 98. As shown in FIG. 4, an extension 100 is created at the bottom of the cavity 98 by use of the drill bit 36 connected to the drill 34. FIG. 5 shows the cavity being circumferentially brushed by the brush 38 connected to the drill 14, and FIG. 6 shows the cavity being irrigated by the syringe 40. After irrigation, as shown in FIG. 7, the cavity is dried by use of the suction tube 58, which is of a length sufficient to reach the bottom of the extension 100 of the cavity 98. The distal tip 62 is small enough to fit into the extension of the cavity 100. The cover 60 of the suction tube 58 is made of a moisture-absorbent material, such as felt, to remove any moisture that may remain in the cavity 98.

Figure 8:
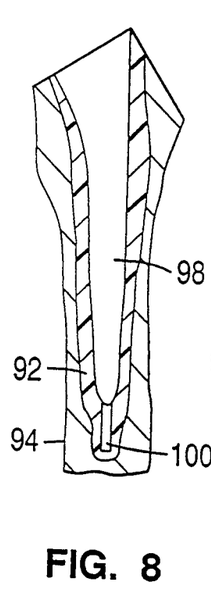
FIG. 8 is a cross-sectional elevational view similar to FIG. 7, illustrating the cavity after it has been prepared for removal of the cement mantle.
Figure 9:
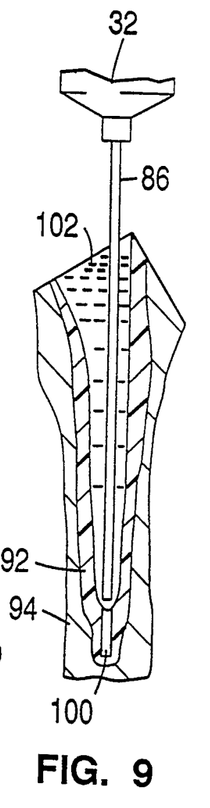
FIG. 9 is a cross-sectional elevational view similar to FIG. 8, illustrating the step of filling the cavity in the cement mantle with fluid cement.

FIG. 8 shows the cavity after these steps, ready for removal of the cement mantle 92. FIG. 9 shows the step of injecting a mass of fluid cement 102 into the cavity 98 by means of the snout 86. The snout 86 is sufficiently small that it may extend to the bottom of extension 100 and provide for venting to enable the extension 100 to be filled with cement. In the preferred embodiment, the fluid cement injected is the same as that from which the mantle was originally fabricated and functions to soften and partially dissolve the mantle. As above, methylmethacrylate cement is most commonly used as the mantle to secure prosthetic devices such as femoral component 88. When this type of cement is added to a hardened mass of the same cement, some dissolution and softening of the hardened mass will occur, such that a single fused mass will result when the fluid mass hardens. Upon filling of the cavity, continued injection of cement functions to apply upward pressure to the snout 86 and the snout is slowly withdrawn, thus forming a void-free mass of cement within the cavity.

Figure 11:
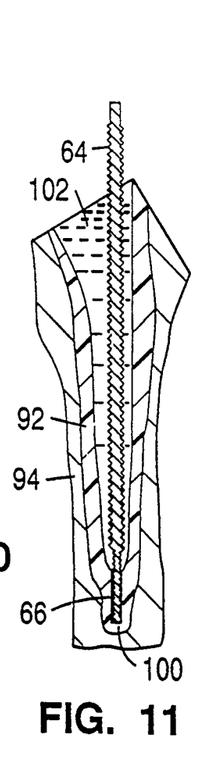
FIG. 11 is a cross-sectional elevational view similar to FIG. 9, illustrating the step of placing the first pulling tool within the fluid cement.

FIG. 11 shows the step of inserting the pulling tool 64 into the cement mass 102 while the mass is still in a fluid state. This is achieved by screwing the threads of the tool into the mass to the point where the distal end 66 engages the extension of the cavity 100, which may be determined by feel, and creates a threaded passageway 104 within the cement mass 102. The screwing of the tool 64 into the fluid mass of cement is carried out in a relatively slow controlled fashion so as to avoid the creation of voids within the mass. This poses no particular problem, since it takes approximately ten minutes for the mass to cure to a hardened state.

Care must be taken to prevent the cement from bonding to the pulling tool as it hardens. This may be accomplished in several ways. The pulling tool may be made of a material which will not bond with the cement, such as certain types of plastic, or it may be coated with a "release" material, such as teflon, silicone mold release, or baked-on silicon.

Figure 12:
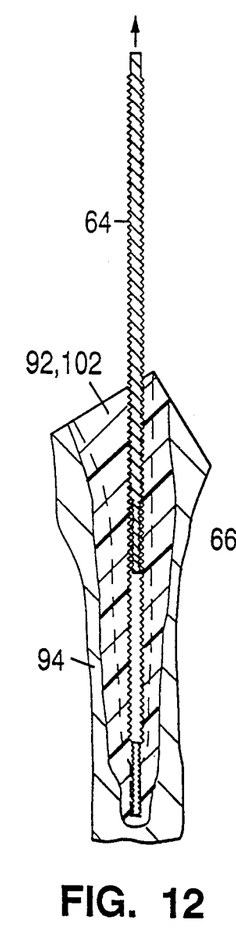
FIG. 12 is a cross-sectional elevational view similar to FIG. 11, illustrating the step of partly removing the first pulling tool from the hardened cement.
Figure 13:
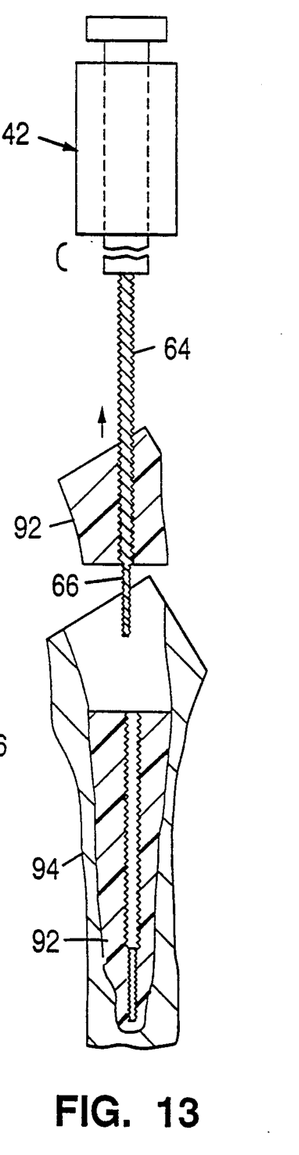
FIG. 13 is a cross-sectional elevational view similar to FIG. 12, illustrating the step of using a slap-hammer to apply tension to the cement mantle through the pulling tool and removing a portion of the cement mantle from the femur.

After the mass of cement 102 has cured to a hardened integral state with the mantle 92, as shown in FIG. 12 the pulling tool 64 is partly removed by unscrewing it from the threaded passageway 104. As shown in FIG. 13, the slap-hammer 42 is then threadably secured to the proximal end of the pulling tool 64, and used to apply impact tension to the pulling tool. Another characteristic of the methylmethacrylate cement is that it has no significant tensile strength. The hardened mass of cement thus shears at the lowest point where the threads of the pulling tool 64 engage the threads of the passageway 104. The use of the slap-hammer thus pulls the tool and the portion of the mantle surrounding the tool from the femur as a unit, leaving behind that portion of the mantle below the lowest point where the threads of the tool engage the threads of the passageway.

Figures 14, 15:
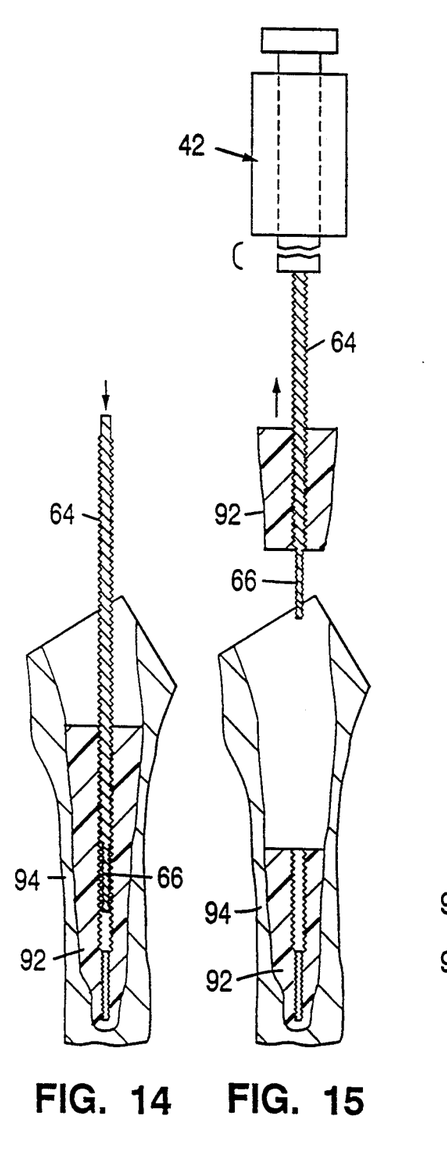
FIG. 14 is a cross-sectional elevational view similar to FIG. 13, illustrating the step of reinserting the pulling tool into the portion of the cement mantle remaining in the femur.
FIG. 15 is a cross-sectional elevational view similar to FIG. 14, illustrating the step of using a slap-hammer to apply tension to the cement mantle through the pulling tool and removing a second portion of the cement mantle from the femur.
Figures 16, 17:
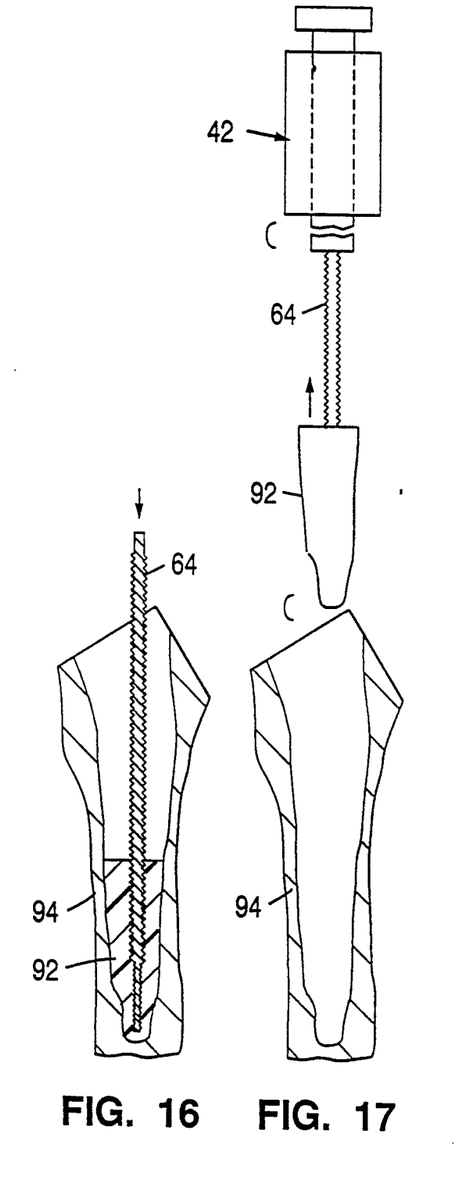
FIG. 16 is a cross-sectional elevational view similar to FIG. 15, illustrating the step of reinserting the pulling tool into the final portion of the cement mantle remaining in the femur.
FIG. 17 is a cross-sectional elevational view similar to FIG. 16, illustrating the step of using a slap-hammer to apply tension to the cement mantle through the pulling tool and removing the final portion of the cement mantle from the femur.

This process may be repeated as many times as desired, so that the mantle is removed in two or more pieces, and removal of each portion of the mantle can be accomplished by a minimum of force from the slap-hammer so as to prevent damage to the femur. Here the mantle is shown being removed in three steps. In FIG. 14, the pulling tool is reinserted into the passageway by screwing it into the portion of the mantle remaining in the cavity. Then, as shown in FIG. 15, the slap hammer is again attached to the pulling tool and a second portion of the mantle is removed. Finally, as shown in FIGS. 16 and 17, the pulling tool is again reinserted into the passageway all the way to the bottom of the extension 100, and the slap-hammer is used to remove the final portion of the cement. This step leaves the original bone cavity, designated 106, within the femur in a clean state. Thereafter, a new prosthetic joint may be cemented into the bone cavity.

FIGS. 19 through 23 sequentially illustrate the steps of an alternative method of removing the cement mantle 92 by use of the second pulling tool 68, which is shown in FIG. 18. The cavity is prepared as previously described and shown in FIGS. 2 through 8. Fluid cement 102 is then injected into the cavity 98 as shown in FIG. 9. While the mass is still in a fluid state, second pulling tool 68 is inserted into the cement mass 102, as shown in FIG. 19, again defining a threaded passageway 104 in the cement mass 102. As before, precautions are taken to prevent the cement from bonding to the pulling tool.

After the cement hardens, the proximal first portion 70 of the second pulling tool 68 is partly removed by unscrewing it from the threaded passageway 104 at least far enough that it separates from the second portion 72, as shown in FIG. 20. Next, as shown in FIG. 21, the slap-hammer 42 is secured to the proximal end of the first portion 70 and used to apply impact tension to it, thus shearing off the methylmethacrylate cement at the point of deepest penetration of the first portion 70, as in the prior embodiment.

Figures 22, 23:
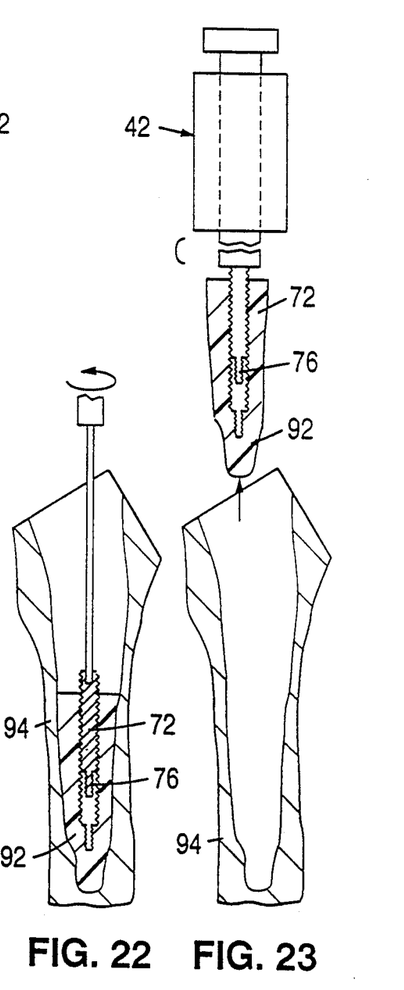
FIG. 22 is a cross-sectional elevational view similar to FIG. 21, illustrating the step of partly removing the distal end of the pulling tool from the portion of the cement mantle remaining in the femur.
FIG. 23 is a cross-sectional elevational view similar to FIG. 22, illustrating the step of using a slap-hammer to apply tension to the cement mantle through the distal end of the pulling tool and removing a second and final portion of the cement mantle from the femur.

The second portion 72 of the pulling tool is then removed from the remaining portion of the cement mantle by unscrewing it just far enough for the slap-hammer 42 to be attached, as shown in FIG. 22. Finally, as shown in FIG. 23, the remaining portion of the mantle is removed.

FIGS. 25 through 29 sequentially illustrate the steps of another alternative method of removing the cement mantle 92 by use of the third pulling tool 78, which is shown in FIG. 24. Again the cavity is prepared as previously described and shown in FIGS. 2 through 8, and fluid cement 102 is injected into the cavity 98 (FIG. 9). While the mass is still in a fluid state, third pulling tool 78 is inserted into the cement mass 102, as shown in FIG. 25, again defining a threaded passageway 104 in the cement mass 102.

After the cement hardens, the proximal first portion 80 of the third pulling tool 78 is partly removed by unscrewing it from the threaded passageway 104 at least far enough that it separates from the second portion 82, as shown in FIG. 26. Since the second portion 82 is only screwed into the receptacle on first portion 80, unscrewing first portion 80 from the passageway also results in unscrewing second portion 82 from the receptacle. Next, as shown in FIG. 27, the slap-hammer 42 is again secured to the proximal end of the first portion 80 and used to apply impact tension to it, again shearing off the methylmethacrylate cement at the point of deepest penetration of the first portion 80, as in the prior embodiments.

Figures 27, 28, 29:
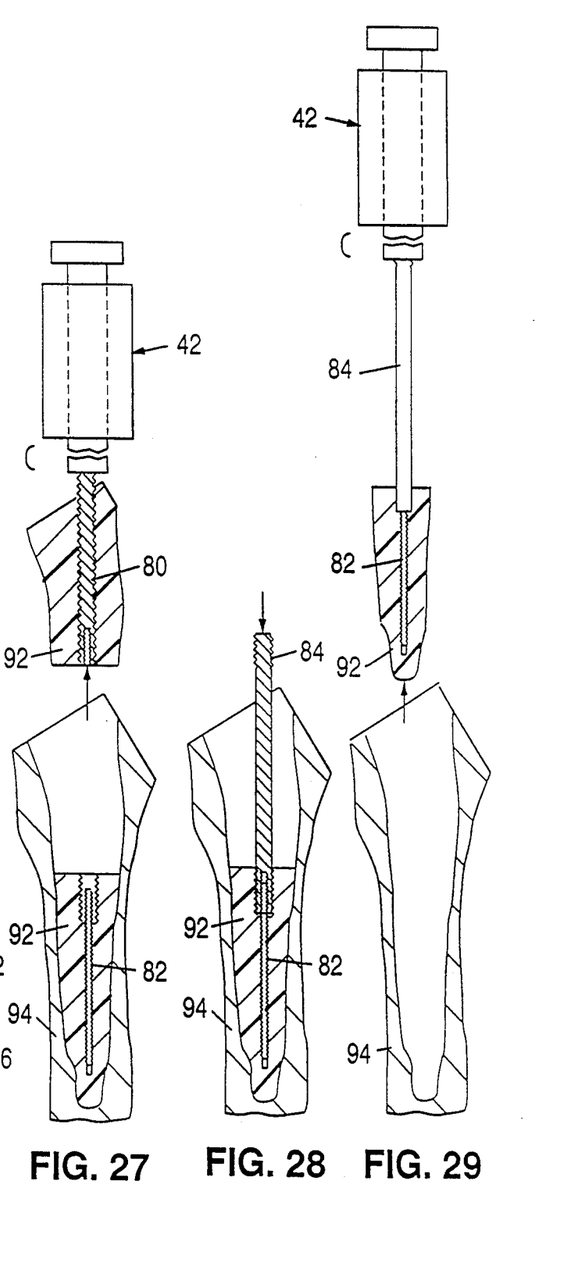
FIG. 27 is a cross-sectional elevational view similar to FIG. 26, illustrating the step of using a slap-hammer to apply tension to the cement mantle through the pulling tool and removing a portion of the cement mantle from the femur.
FIG. 28 is a cross-sectional elevational view similar to FIG. 27, illustrating the step of attaching a connecting rod to the distal end of the pulling tool in the portion of the cement mantle remaining in the femur.
FIG. 29 is a cross-sectional elevational view similar to FIG. 28, illustrating the step of using a slap-hammer to apply tension to the cement mantle through the connecting rod and the distal end of the pulling tool and removing a second and final portion of the cement mantle from the femur.

The second portion 82 of the pulling tool need not be removed from the remaining portion of the cement mantle, because it already extends into the wider part of the threaded passageway 104 left by removal of the first portion 80, as can be seen in FIGS. 26 and 27. Now the connecting tool 84 can be attached to the proximal end of second portion 82 by screwing it thereon., as shown in FIG. 28. Since the outside diameter of the connecting tool 84 is less than the inside diameter of the threaded passageway 104, the tool need only be screwed onto the second portion 82 and need not be screwed all the way into the passageway. Finally, the slap-hammer 42 is again attached to the tool 84, and the remaining portion of the mantle is removed as shown in FIG. 22.

Numerous variations on these embodiments are possible. For example, to prevent the fluid cement from bonding to the pulling tool as it hardens, it is possible to use a light plastic post to form the threaded passageway, even if it is of insufficient strength to serve as the pulling tool, and then replace it with a steel pulling tool of the same configuration once the cement has hardened. Here the plastic post need not have a detachable distal end, even if the pulling tool is of the second or third types described above, since the plastic will be removed and not used in the steps of actually removing the cement mantle. In addition, the process can be broken into even more steps so that smaller pieces of the mantle are removed with each use of the slap-hammer, if this is necessary to insure that the force applied can be kept small enough so as not o damage the surrounding bone.

From the above description, it will be apparent that the invention disclosed herein provides a novel and advantageous method and apparatus for removing preplaced prosthetic joints and preparing for their replacement. The foregoing discussion discloses and describes merely exemplary methods and embodiments of the present invention. As will be understood by those familiar with the art, the invention may be embodied in other specific forms without departing from the spirit or essential characteristics thereof. For example, it is anticipated that the invention may find use in the removal of a cement mantle in other than a joint replacement application and that it may be used in replacing joints other than hip joints. Accordingly, the disclosure of the present invention is intended to be illustrative, but not limiting, of the scope of the invention, which is set forth in the following claims.

What is claimed is:

1. A surgical pulling tool sized for embedment within a mass of cement disposed in a bone cavity to remove the cement from the bone cavity, said surgical tool comprising:
    (a) a first rigid cylindrical post having proximal and distal ends, and having an exterior surface of a helical screw thread formed around said post;
    (b) a second rigid cylindrical post attached to the distal end of said first post, said second post being of reduced diameter as compared to said first post and extending axially therefrom;
    (c) means on said proximal section for securing a slap-hammer to said first post;
    (d) wherein the second helical screw thread formed around said second post is of the same pitch as the helical screw thread formed around said first post.

2. A surgical pulling tool according to claim 1, wherein said first post comprises a proximal section and a distal section, and further comprising means for detaching said proximal section from said distal section.

3. A surgical pulling tool according to claim 2, wherein said means for detaching said proximal section from said distal section comprises:
    (a) a cylindrical extension of smaller diameter than the post formed upon one said section of the post; and
    (b) a recess for frictional receipt of said extension formed upon the other said section of the post.

4. A surgical pulling tool according to claim 1, further comprising means for detaching said second post from said first post.

5. A surgical pulling tool according to claim 4, wherein said means for detaching said second post from said first post comprises a recess in said first post which is threaded for receipt of said second post such that the posts may be detached by unscrewing said second post from said recess.

* * * * *